US009850521B2

United States Patent
Braman et al.

(10) Patent No.: US 9,850,521 B2
(45) Date of Patent: Dec. 26, 2017

(54) IN VITRO ASSAY BUFFER FOR CAS9

(71) Applicant: Agilent Technologies, Inc., Loveland, CA (US)

(72) Inventors: Jeffrey Carl Braman, Carlsbad, CA (US); Yuchu Grace Hsiung, San Diego, CA (US); Katherine Felts, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 10 days.

(21) Appl. No.: 14/727,479

(22) Filed: Jun. 1, 2015

(65) Prior Publication Data

US 2016/0032353 A1 Feb. 4, 2016

Related U.S. Application Data

(60) Provisional application No. 62/032,332, filed on Aug. 1, 2014.

(51) Int. Cl.
*C12Q 1/44* (2006.01)

(52) U.S. Cl.
CPC .................... *C12Q 1/44* (2013.01)

(58) Field of Classification Search
CPC ........................................ C12Q 1/44
See application file for complete search history.

(56) References Cited

U.S. PATENT DOCUMENTS

| 6,923,988 B2 * | 8/2005 | Patel | A61K 9/1617 424/422 |
| 8,518,450 B2 * | 8/2013 | Kalombo | A61K 9/5123 424/489 |
| 2014/0179770 A1 * | 6/2014 | Zhang | C12N 15/86 514/44 R |

OTHER PUBLICATIONS

Pattanayak et al., High-throughput profiling of off-target DNA cleavage reveals RNA-programmed Cas9 nuclease specificity, nature biotechnology, vol. 31, No. 9, Sep. 2013.*

Jurek et al., Nanoparticles Preparation Using Microemulsion Systems, Ch. 12, Microemulsions—An Introduction to Properties and Applications, (2012), published by InTech: ISBN: 978-953-51-0247-2, Available from: http://www.intechopen.com/books/microemulsions-an-introduction-to-properties-andapplications/nanoparticles-preparation-using-mic.*

Dicarlo, et al., "Genome engineering in *Saccharomyces cerevisiae* using CRISPR-Cas systems", Nucleic Acids Research, 2013, vol. 41, No. 7, pp. 4336-4343.

Gasiunas, et al., "Cas9-crRNA ribonucleoprotein complex mediates specific DNA cleavage for adaptive immunity in bacteria", PNAS, 2012, pp. E2579-E2586.

Hwang, et al., "Efficient In Vivo Genome Editing Using RNA-Guided Nucleases", Nat Biotechnol. 2013: 31(3), pp. 227-229.

Jiang, et al., "CRISPR-assisted editing of bacterial genomes", Nat Biotechnol. Mar. 2013; 31(3), pp. 233-239.

Jinek, et al., "RNA-programmed genome editing in human cells", eLife, 2013;2:e00471, pp. 1-9.

(Continued)

*Primary Examiner* — Reza Ghafoorian

(57) ABSTRACT

Provided herein is a reaction mixture comprising Cas9 and a non-ionic surfactant, e.g., a polyoxyethylene surfactant. In certain embodiments, the reaction mixture may comprise a Cas9 protein, a guide RNA, a salt, a buffering agent, a nucleic acid target and a non-ionic surfactant. Kits are also provided. In certain embodiments, a kit may comprise: a Cas9 protein; and a concentrated reaction buffer comprising salt, a buffering agent and a non-ionic surfactant.

20 Claims, 5 Drawing Sheets

(56) References Cited

OTHER PUBLICATIONS

Karvelis, et al., "Programmable DNA cleavage in vitro by Cas9", Biochem. Soc. Trans, (2013) 41, 1pp. 401-1406.
Lecong, et al., "Multiplex Genome Engineering Using CRISPR/Cas Systems", Science, 2013; 339(6121), pp. 819-823.
Mali, et al., "RNA-Guided Human Genome Engineering via Cas9", Science, 2013, 339(6121), pp. 823-826.
Pattanayak, et al., "High-throughput profiling of off-target DNA cleavage reveals RNA-programmed Cas9 nuclease specificity", Nat Biotechnol, 2013; 31(9), pp. 839-843.
Qi, et al., "Repurposing CRISPR as an RNA-Guided Platform for Sequence-Specific Control of Gene Expression", Cell, 2013; 152(5), pp. 1173-1183.

* cited by examiner

| ng Cas9/rxn | % target cleaved | avg | Q-test (90% confidence) Qcrit Value=0.94 @N=3 |
|---|---|---|---|
| 40 | 92.26% | 92.11% | |
| 40 | 91.59% | | |
| 40 | 92.49% | | |
| 30 | 91.64% | 89.16% | |
| 30 | 89.89% | | |
| 30 | 85.96% | | |
| 25 | 84.61% | 83.21% | 0.1901 |
| 25 | 85.89% | | |
| 25 | 79.14% | | |
| 20 | 68.45% | 66.61% | 0.0574 |
| 20 | 68.80% | | |
| 20 | 62.57% | | |
| 15.1 | 52.20% | 50.49% | 0.0020 |
| 15.1 | 52.19% | | |
| 15.1 | 47.08% | | |
| 11 | 34.96% | 34.14% | 0.0158 |
| 11 | 34.92% | | |
| 11 | 32.54% | | |
| 5.48 | 17.31% | 16.76% | 0.2094 |
| 5.48 | 17.03% | | |
| 5.48 | 15.95% | | |
| 0 | 0.00% | 0.00% | 0.0000 |
| 0 | 0.00% | | |
| 0 | 0.00% | | |

FIG. 3

IN VITRO ASSAY BUFFER FOR CAS9

CROSS-REFERENCE TO RELATED APPLICATION

This application claims the benefit of U.S. provisional application Ser. No. 62/032,332, filed on Aug. 1, 2014, which application is hereby incorporated by reference herein in its entirety.

BACKGROUND

Cas9 (CRISPR associated protein 9) is an RNA-guided DNA nuclease associated with the Type II bacterial CRISPR immunity system. Cas9 can be used in vitro and in vivo to induce site-specific double stranded breaks in DNA. In most cases, the RNA guide structure that binds and directs Cas9 is a hybrid of CRISPR RNA, containing homologous sequence to the cleavage target, and a trans-activating "tracr" RNA. A single guide RNA "sgRNA" chimera of the CRISPR (Cr) and tracr RNAs can direct DNA cleavage by Cas9 in vitro.

SUMMARY

Provided herein is a reaction mixture comprising Cas9 and a non-ionic surfactant, e.g., a polyoxyethylene surfactant. In certain embodiments, the reaction mixture may comprise a Cas9 protein, a guide RNA, a salt, a buffering agent, a nucleic acid target and a non-ionic surfactant. Kits are also provided. In certain embodiments, a kit may comprise: a Cas9 protein; and a concentrated reaction buffer comprising salt, a buffering agent and a non-ionic surfactant.

BRIEF DESCRIPTION OF THE FIGURES

FIG. 3 is a table of the numerical results represented by the image in FIG. 1 and on the graph shown in FIG. 2.

DEFINITIONS

Figure 1:
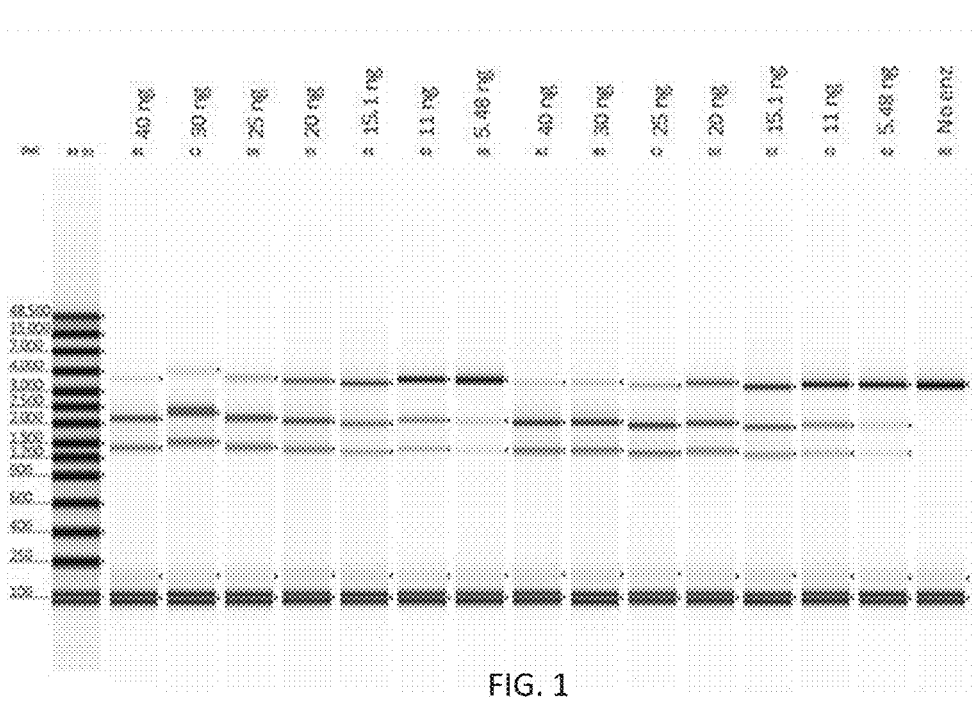
FIG. 1 is an Agilent Screen Tape image showing Cas9 digestion of KS-kan C1 DNA target.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150, 150 to 200, or 200 to 250 nucleotides in length, for example.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

The term "target sequence" refers to a sequence in a double-stranded DNA molecule, where the target sequence is bound, and, optionally cleaved or nicked by Cas9. In many cases, a target sequence may be unique in any one starting molecule and, as will be described in greater detail below, multiple different starting molecules (e.g., overlapping fragments) may contain the same target sequence. In some cases, the target sequence may be degenerate, that is, the target sequence may have base positions that may have variable bases. These positions may be denoted as Y, R, N, etc., where Y and R denote pyrimidine and purine bases, respectively, and N denotes any of the 4 bases.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "nicking," as used herein, refers to a reaction that breaks the phosphodiester bond between two nucleotides in one strand of a double-stranded DNA molecule to produce a 3' hydroxyl group and a 5' phosphate group.

The term "Cas9-associated guide RNA" refers to a guide RNA as described above (comprising a crRNA molecule and a tracrRNA molecule, or comprising an RNA molecule that includes both crRNA and tracrRNA sequences). The Cas9-associated guide RNA may exist as isolated RNA, or as part of a Cas9-gRNA complex.

Reference to a Cas9-associated guide RNA being "complementary to" another sequence is not intended to mean that the entire guide RNA is complementary to the other sequence. A Cas9-associated guide RNA that is complementary to another sequence comprises a sequence that is complementary to the other sequence. Specifically, it is known that a Cas9 complex can specifically bind to a target sequence that has as few as 8 or 9 bases of complementarity with the guide Cas9-associated guide RNA in the complex. Off-site binding can be decreased by increasing the length of complementarity, e.g., to 15 or 20 bases.

The terms "Cas9 enzyme" and "Cas9-gRNA complex" refer to a complex comprising a Cas9 protein and a guide RNA (gRNA). The guide RNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a sgRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas9 protein, or only one or some of the functions, including binding activity and nuclease activity.

For Cas9 to successfully bind to DNA, the target sequence in the genomic DNA should be complementary to the gRNA sequence and must be immediately followed by the correct proto-spacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type II CRISPR system is derived from *S. pyogenes* and the PAM sequence is NGG located on the immediate 3' end of the gRNA recognition sequence. The PAM sequences of Type II CRISPR systems from exemplary bacterial species include: *Streptococcus pyogenes* (NGG), *Neisseria meningitidis* (NNNNGATT), *Streptococcus thermophilus* (NNAGAA) and *Treponema denticola* (NAAAAC).

The term "Cas9 nickase" refers to a modified version of the Cas9-gRNA complex, as described above, containing a single inactive catalytic domain, i.e., either the RuvC- or the HNH-domain. With only one active nuclease domain, the Cas9 nickase cuts only one strand of the target DNA, creating a single-strand break or "nick". A Cas9 nickase is still able to bind DNA based on gRNA specificity, though nickases will only cut one of the DNA strands. The majority of CRISPR plasmids currently being used are derived from *S. pyogenes* and the RuvC domain can be inactivated by an amino acid substitution at position D10 (e.g., D10A) and the HNH domain can be inactivated by an amino acid substitution at position H840 (e.g., H840A), or at positions corresponding to those amino acids in other proteins. As is known, the D10 and H840 variants of Cas9 cleave a Cas9-induced bubble at specific sites on opposite strands of the DNA. Depending on which mutant is used, the guide RNA-hybridized strand or the non-hybridized strand may be cleaved.

The term "mutant Cas9 protein that has inactivated nuclease activity" refers to a Cas9 protein that has inactivated HNH and RuvC nucleases. Such a protein can bind to a target site in double-stranded DNA (where the target site is determined by the guide RNA), but the protein is unable to cleave or nick the double-stranded DNA.

As used herein and unless indicated to the contrary, the term "Cas9-fragment complex" refers to a complex containing a Cas9-gRNA and a DNA fragment to which the Cas9-gRNA complex binds.

As used herein, a "polyoxyethylene" surfactant has a neutral, polar head group and one or more hydrophobic tails that contain an oxyethylene polymers of formula $(CH_2CH_2O)_n$. Many polyoxyethylene surfactants are of the formula $RX(CH_2CH_2O)_nH$, where R is H (for polyethylene glycols), hydroxyl or a hydrophobic group (e.g., $C_1$-$C_{20}$) and X is a hetero atom such as O (for polyoxyethylene alcohols), N (for polyoxyethylene alkylamines or polyoxyethylene alkylamides), S (for polyoxyethylene mercaptans), or phenol (for polyoxyethylene alkylphenols). Brij series surfactants, Triton series surfactants, Tween series surfactants, Surfynol series surfactants and Tergitol series surfactants are examples of polyoxyethylene surfactants.

As used herein, "Brij series" surfactants are polyoxyethylene glycol alkyl ethers of the formula $CH_3$—$(CH_2)_{10-16}$—$(O$—$C_2H_4)_{1-25}$—OH. Examples of Brij series surfactants include octaethylene glycol monododecyl ether and pentaethylene glycol monododecyl, as well as Brij-35, Brij-56, Brij-58.

As used herein, "Triton series" surfactants are polyoxyethylene glycol octylphenol ethers defined by the formula $C_8H_{17}$—$(C_6H_4)$—$(O$—$C_2H_4)_{1-25}$—OH and include Triton X-114, Triton X-100, Triton X-102 & Triton X-165.

As used herein, "Tween series" surfactants are polyoxyethylene glycol sorbitan alkyl esters and include polysorbates known as Tween 20 and Tween 80.

As used herein, "Surfynol" surfactants are defined by the following formula, where n1 and n2 are independently 5-30. For Surfynol 465, for example, n1=n2=10.

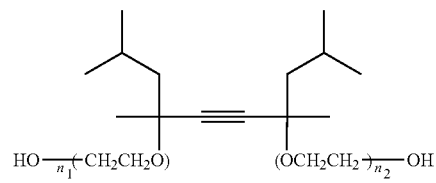

As used herein, "Tergitol" surfactants are defined by the following formula, where n, n1 and n2 are independently 5-30. For Tergitol 15-S-5, for example, n+n1=12, n2=4; for Tergitol 15-S-7, n+n1=12 and n2=6; and for Tergitol 15-S-9, n+n1=12 and n2=8. Further examples of polyoxyethylene include Nonoxynol-9, Nonidet P-40, and Igepal series surfactants although many others are known.

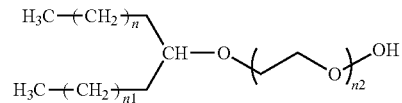

As used herein, "glycosidic" surfactants are surfactants that have a carbohydrate, typically glucose or maltose as the polar head group and an alkyl chain length of 7-14 carbons as the nonpolar tail. Glucoside alkyl ethers can be of the formula $CH_3$—$(CH_2)_{10-16}$—(O-Glucoside)$_{1-3}$-OH, and examples include glucoside alkyl ethers such as decyl glucoside, lauryl glucoside and octyl glucoside.

As used herein, "bile salt" surfactants have a steroid core structure.

As used herein the term "hydrophilic/lipophilic balance" (HLB) is calculated by the Griffin method using the formula:

$$HLB = 20 * Mh/M$$

where Mh is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule. Further details of Griffin's method can be found in Griffin (Journal of the Society of Cosmetic Chemists 1949 1: 311-326) and Griffin (Journal of the Society of Cosmetic Chemists 1954 5: 249-256) which are incorporated by reference.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The following references are explicitly incorporated by reference for their teachings on Cas9, gRNA, and other reagents that can be used herein: Gasiunas et al (Proc. Natl. Acad. Sci. 2012 109: E2579-E2586), Karvelis et al (Biochem. Soc. Trans. 2013 41:1401-6), Pattanayak et al (Nat. Biotechnol. 2013 31: 839-43), Jinek et al. (Elife 2013 2: e00471), Jiang et al (Nat. Biotechnol. 2013 31:233-9), Hwang et al (Nat. Biotechnol. 2013 31: 227-9), Mali et al (Science 2013 339:823-6), Cong et al (Science. 2013 339: 819-23), DiCarlo et al (Nucleic Acids Res. 2013 41: 4336-43) and Qi et al (Cell. 2013 152: 1173-83).

As would be appreciated, the compositions and kits described below may be employed to fragment a wide variety of different types of DNA, including plasmids, cDNA, genomic DNA and PCR products.

Reaction Mixtures

As noted above, provided herein is a reaction mixture comprising: a) a Cas9 protein; b) a guide RNA; c) a salt; d) a buffering agent; e) a target nucleic acid; and f) a non-ionic surfactant. In some embodiments, the presence of the surfactant increases the rate of cleavage of the target nucleic acid by at least 5% (e.g., at least 10%, at least 15%, at least 20%, at least 25%, up to 50%, up to 80% or up to 100% or more, up to 200% or more).

As would be apparent, this reaction is in vitro, i.e., in a cell-free environment, and the target nucleic acid in the sample may be from any source, including but not limited to total genomic DNA and complementary DNA (cDNA), plasmid DNA, mitochondrial DNA, synthetic DNA, BAC clones, PCR products, etc. The target nucleic acid may be from any organism, including, but not limited to a prokaryote and a eukaryote. In certain cases, the organism may be a plant, e.g., *Arabidopsis* or maize, or an animal, including reptiles, mammals, birds, fish, and amphibians. In some cases, the test genome may be human or rodent, such as a mouse or a rat. Methods of preparing genomic DNA for analysis is routine and known in the art, such as those described by Ausubel, F. M. et al., (*Short protocols in molecular biology*, 3rd ed., 1995, John Wiley & Sons, Inc., New York) and Sambrook, J. et al. (*Molecular cloning: A laboratory manual*, $2^{nd}$ ed., 1989, Cold Spring Harbor Laboratory Press, Cold Spring Harbor, New York). In certain cases, the sample used may contain total genomic DNA, which may be unamplified or amplified, e.g., genomic DNA that has been amplified by a whole genome amplification method that may or may not be already fragmented by other means. In other embodiments, the target nucleic acid may be a PCR product or plasmid, methods for the production of which are well known.

The Cas9-gRNA complexes may comprise a set of at least 10, at least 100, at least 1,000, at least 10,000, at least 50,000 or at least 100,000 or more different Cas9-associated guide RNAs. In certain cases the guide RNAs are each complementary to a different, pre-defined site in a genome.

The amount of Cas9 present in the reaction mixture may vary greatly. However, in some cases, the reaction mixture may contain 0.1 U-50 U, e.g., 0.5 U to 20 U, of enzyme, wherein 1 unit of Cas9 is the amount of Cas9 required to provide 50% cleavage of the target nucleic acid under the conditions used.

In some embodiments, the buffering agent may be Tris (tris(hydroxymethyl)aminomethane), HEPES ((4-(2-hydroxyethyl)-1-piperazineethanesulfonic acid)), TAPS (3-{[tris(hydroxymethyl)methyl]amino}propanesulfonic acid), MOPS (3-(N-morpholino)propanesulfonic acid), tricine (N-tris(hydroxymethyl)methylglycine) or MES (2-(N-morpholino)ethanesulfonic acid).

In some embodiments, the buffering agent may be at a concentration of 1 mM to 50 mM, e.g., 5 mM to 20 mM.

In some embodiments, the pH of the reaction mixture may be in the range of pH 5 to 8.5, e.g., pH 6.5 to pH 8.0.

In some embodiments, the reaction mixture comprises one or more of NaCl, $MgCl_2$, $MgSO_4$ and KCl.

In some embodiments, the salt in the reaction mixture may be at a concentration in the range of 1 mM to 500 mM, e.g., 10 mM to 250 mM.

In some embodiments, the reaction mixture comprises NaCl at a concentration 10 mM to 250 mM and $MgCl_2$ at a concentration of 1 mM to 50 mM.

In some embodiments, the non-ionic surfactant is present in the reaction mixture at a concentration in the range of 0.005% to 1%, e.g., 0.01 to 0.5%, or 0.025 to 0.2% v/v.

In some embodiments, the non-ionic surfactant may be a polyoxyethylene (e.g., ethoxylated acetylenic diol) or polyoxypropylene surfactant.

In some embodiments the polyoxyethylene surfactant is a Brij series surfactant, a Triton series surfactant, a Tween series surfactant, a Surfynol series surfactant, a Tergitol series surfactant.

In some embodiments the non-ionic surfactant is a glycosidic surfactant or a bile salt surfactant.

In some embodiments, the non-ionic surfactant used has an HLB in the range of 12-15, e.g., an HLB in the range of 12.5-13.5.

In some embodiments the non-ionic surfactant having an HLB in the range of 12-15 is selected from Triton X-100 (HLB=13.5), Triton® SP-190 (HLB=13), Triton XL-80N (HLB 12.5), Surfynol 465 (HLB=13), Tergitol 15-S-7 (HLB=12.1), 15-S-9 (HLB=13.9), 15-S-12 (HLB=14.5), Tergitol NP-9 (HLB=12.9), Sulonic JL-80X (HLB=13.1), Ethofat 242/25 (HLB=12.1), IGEPAL® CA-720 (HLB=14) and Lutensol NP 10 (HLB=14.0).

In some embodiments, the non-ionic surfactant may be selected from: the TERGITOL® series (alkyl polyethylene oxides) available from Union Carbide Co. (Houston, Tex.) such as Tergitol 15-S-5, 15-S-7; the BRIJ series (poly-ethoxylated alcohols and esters) such as Brij 30 available from ICI Americas (Wilmington, Del.); the SURFYNOL® series (acetylenic polyethylene oxides) such as Surfynol 104 (2,4,7,9-tetramethyl-5-decyne-4,7-diol), Surfynol 400 series such as Surfynol 440, and Surfynol CT series, such as Surfynol CT-111 and CT-211 (as shown and described below) (available from Air Products (Allentown, Pa.); DYNOL® 604 (an ethoxylated acetylenic diol mixture) from Air Products and Chemicals Inc. (Allentown, Pa.); the TRITON series (alkyl phenyl polyethylene oxides) such as Triton X-45 available from Rohm & Haas (Philadelphia, Pa.) and those available from Dow Chemical Corporation (Midland, Mich.) such as TRITON® X-100 (an octylphe-noxypolyethoxyethanol); Aerosol OT (a sodium dioctyl sul-fosuccinate) from CYTEC Industries (West Paterson, N.J.); WITCONATE P-1059 (an alkaryl sulfonate isopropylamine salt) from CK Witco Corporation (Houston, Tex.).

In some embodiments, the non-ionic surfactant may be selected from: cetomacrogol 1000, cetostearyl alcohol, cetyl alcohol, cocamide DEA, cocamide MEA, decyl glucoside, IGEPAL CA-630, isoceteth-20, lauryl glucoside, monolau-rin, an ethoxylate, nonidet P-40, nonoxynol-9, nonoxynols, NP-40 octaethylene glycol monododecyl ether, N-Octyl beta-D-thioglucopyranoside, octyl glucoside, oleyl alcohol, pentaethylene glycol monododecyl ether, poloxamer, polox-amer 40, polyglycerol polyricinoleate, polysorbate 20, poly-sorbate 80, sorbitan monostearate, sorbitan tristearate, stearyl alcohol, Triton X-100 and Tween 20, as well as functionally equivalent derivatives of the same.

Kits

Also provided herein are kits. A subject kit may contain: a) a Cas9 protein; and b) a concentrated reaction buffer comprising salt, a buffering agent and a non-ionic surfactant. The Cas9 may be in glycerol at a concentration of, e.g., 10-80%, e.g., 40-60%.

The subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kit as a package insert, in the labeling of the container of the kit or components thereof (i.e., associated with the packaging or subpackaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The various components of the kit may be in separate containers, where the containers may be contained within a single housing, e.g., a box.

In some embodiments, the kit can further comprise a guide RNA or construct for making the same by in vitro transcription.

In some embodiments, the kit can further comprise an RNAse-free water.

In some embodiments, the concentrated reaction buffer may be a 5x or 10x concentrate.

In some embodiments, the buffering agent may be Tris (tris(hydroxymethyl)aminomethane), HEPES ((4-(2-hy-droxyethyl)-1-piperazineethanesulfonic acid)), TAPS (3-{[tris(hydroxymethyl)methyl]amino}propanesulfonic acid), MOPS (3-(N-morpholino)propanesulfonic acid), tricine (N-tris(hydroxymethyl)methylglycine) or MES (2-(N-morpholino)ethanesulfonic acid).

In some embodiments, the concentrated reaction buffer is formulated such that, when the concentrated reaction buffer is diluted to a 1x concentration, the 1x reaction buffer comprises a buffering agent at a concentration of 1 mM to 50 mM, e.g., 5 mM to 20 mM.

In some embodiments, the concentrated reaction buffer is formulated such that, when the concentrated reaction buffer is diluted to a 1x concentration, the 1x reaction buffer has a pH in the range of pH 5 to 8.5, e.g., pH 6.5 to pH 8.0.

In some embodiments, the concentrated reaction buffer comprises one or more of NaCl, $MgCl_2$, $MgSO_4$ and KCl.

In some embodiments, the concentrated reaction buffer is formulated such that, when the concentrated reaction buffer is diluted to a 1x concentration, the 1x reaction buffer comprises a salt at a concentration in the range of 1 mM to 500 mM, e.g., 10 mM to 250 mM.

In some embodiments, the concentrated reaction buffer is formulated such that, when the concentrated reaction buffer is diluted to a 1x concentration, the 1x reaction buffer comprises NaCl at a concentration of 10 mM to 250 mM and $MgCl_2$ at a concentration of 1 mM to 50 mM.

In some embodiments, the concentrated reaction buffer is formulated such that, when the concentration reaction buffer is diluted to a 1x concentration, the 1x reaction buffer comprises a non-ionic surfactant at a concentration in the range of 0.005% to 1%, e.g., 0.01 to 0.5% or 0.025 to 0.2%.

In some embodiments, the non-ionic surfactant may be a polyoxyethylene or polyoxypropylene surfactant.

In some embodiments the polyoxyethylene surfactant is a Brij series surfactant, a Triton series surfactant, a Tween series surfactant, a Surfynol series surfactant, a Tergitol series surfactant.

In some embodiments the non-ionic surfactant is a gly-cosidic surfactant or a bile salt surfactant.

In some embodiments, the non-ionic surfactant used has an HLB in the range of 12-15, e.g., in the range of 12.5-13.5.

In some embodiments, the non-ionic surfactant having an HLB in the range of 12-15 is selected from Triton X-100 (HLB=13.5), Triton® SP-190 (HLB=13), Triton XL-80N (HLB 12.5), Surfynol 465 (HLB=13), Tergitol 15-S-7 (HLB=12.1), 15-S-9 (HLB=13.9), 15-S-12 (HLB=14.5), Tergitol NP-9 (HLB=12.9), Sulonic JL-80X (HLB=13.1), Ethofat 242/25 (HLB=12.1), IGEPAL® CA-720 (HLB=14) and Lutensol NP 10 (HLB=14.0).

In some embodiments, the non-ionic surfactant may be selected from: the TERGITOL® series (alkyl polyethylene oxides) available from Union Carbide Co. (Houston, Tex.)

such as Tergitol 15-S-5, 15-S-7; the BRIJ series (polyethoxylated alcohols and esters) such as Brij 30 available from ICI Americas (Wilmington, Del.), the SURFYNOL® series (acetylenic polyethylene oxides) such as Surfynol 104 (2,4,7,9-tetramethyl-5-decyne-4,7-diol), Surfynol 400 series such as Surfynol 440, and Surfynol CT series, such as Surfynol CT-111 and CT-211 (as shown and described below) (available from Air Products (Allentown, Pa.); DYNOL® 604 (an ethoxylated acetylenic diol mixture) from Air Products and Chemicals Inc. (Allentown, Pa.); the TRITON series (alkyl phenyl polyethylene oxides) such as Triton X-45 available from Rohm & Haas (Philadelphia, Pa.) and those available from Dow Chemical Corporation (Midland, Mi) such as TRITON® X-100 (an octylphenoxypolyethoxyethanol); Aerosol OT (a sodium dioctyl sulfosuccinate) from CYTEC industries (West Paterson, N.J.); WITCONATE P-1059 (an alkaryl sulfonate isopropylamine salt) from CK Witco Corporation (Houston, Tex.).

In some embodiments, the non-ionic surfactant may be selected from: cetomacrogol 1000, cetostearyl alcohol, cetyl alcohol, cocamide DEA, cocamide MEA, decyl glucoside, IGEPAL CA-630, isoceteth-20, lauryl glucoside, monolaurin, an ethoxylate, nonidet P-40, nonoxynol-9, nonoxynols, NP-40 octaethylene glycol monododecyl ether, N-Octyl beta-D-thioglucopyranoside, octyl glucoside, oleyl alcohol, pentaethylene glycol monododecyl ether, poloxamer, poloxamer 40, polyglycerol polyricinoleate, polysorbate 20, polysorbate 80, sorbitan monostearate, sorbitan tristearate, stearyl alcohol, Triton X-100 and Tween 20, as well as functionally equivalent derivatives of the same.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

EXAMPLES

Aspects of the present teachings can be further understood in light of the following examples, which should not be construed as limiting the scope of the present teachings in any way.

Example 1

Bpi Cas9 Unit Determination Assay

The assay consists of cleavage assay by a dilution series of Cas9 enzyme and subsequent analysis of the cleavage efficiency of each reaction. Based on these data the concentration required to achieve 50% cleavage is calculated. Please note that this concentration (defined as 1 unit) is specific to the guide RNA used.

Diluting Cas9 Using 1× Reaction Buffer as Diluent
Make dilutions as the following:
125 ng/µL→12.5× dilution (10 ng/µL)
10 ng/µL→1.33× dilution (7.55 ng/µL)
7.55 ng/µL→1.2× dilution (6.29 ng/µL)
6.29 ng/µL→1.25× dilution (5 ng/µL)
5 ng/µL→1.33× dilution (3.77 ng/µL)
3.77 ng/µL→1.38× dilution (2.74 ng/µL)
2.74 ng/µL→2× dilution (1.37 ng/µL)

Example of making the dilutions:

| Tube # | Target concentration ng/µL | Enz (µL) | 1X diluent (µL) |
|---|---|---|---|
| 1 | 10 | 10 µL of 125 ng/µL | 115 |
| 2 | 7.55 | 80 µL of 10 ng/µL | 26 |
| 3 | 6.29 | 80 µL of 7.55 ng/µL | 16 |
| 4 | 5 | 80 µL of 6.29 ng/µL | 20 |
| 5 | 3.77 | 80 µL of 5 ng/µL | 26 |
| 6 | 2.74 | 80 µL of 3.77 ng/µL | 30 |
| 7 | 1.37 | 80 µL of 2.74 ng/µL | 80 |

Set up reaction as in the table below:
Make reaction master mix:

|  | 1X | 25X |
|---|---|---|
| water | 11 mL | 275 mL |
| 10X Digestion Buffer | 2 mL | 50 mL |
| 50 ng/uL KanC1 template | 2 mL | 50 mL |
| 1 uM KanC guide | 1 mL | 25 mL |
| diluted Cas9 | 4 mL |  |
| total | 20 mL |  |

Aliquot 16 µL into 0.2-mL PCR strip tubes, 24 total.
Perform the reactions in triplicate: row A (1-8), B (1-8) and C (1-8).

|  | 1 | 2 | 3 | 4 | 5 | 6 | 7 | 8 |
|---|---|---|---|---|---|---|---|---|
| A | 10 ng/µL | 7.55 ng/µL | 6.29 ng/µL | 5 ng/µL | 3.77 ng/µL | 2.74 ng/µL | 1.37 ng/µL | 1X diluent |
| B | 10 ng/µL | 7.55 ng/µL | 6.29 ng/µL | 5 ng/µL | 3.77 ng/µL | 2.74 ng/µL | 1.37 ng/µL | 1X diluent |
| C | 10 ng/µL | 7.55 ng/µL | 6.29 ng/µL | 5 ng/µL | 3.77 ng/µL | 2.74 ng/µL | 1.37 ng/µL | 1X diluent |

Add 4 µL of diluted Cas9 to the corresponding tubes.
Perform set up on ice.
Transfer 8-well strip and incubate using the following program:
30 minutes at 30° C.
15 minutes at 65° C.
Keep at 4° C.
Note: if the above program is added as a PCR profile, keep the reactions on ice until the warm up period is finished
Analysis on Agilent Tape Station
Aliquot 3 µL genomic DNA ladder to the first well, and 10 µL of sample buffer from the Tape station genomic DNA reagent into the rest of the wells of an 8-well strip. Add 1 µL of Cas9 digest to pre-dispensed loading buffer. Vortex for >10 seconds, spin to collect samples on bottom of wells and load on genomic screen tape in Tape station.

Digestion of the linearized KS-kan C1 (2973 bps) results in an 1800 bp and a 1173 bp fragments (see FIG. 1). For analysis of data export, results to an Excel file. The output file will list sizes and amounts for the fragments generated by the digest. The cleavage efficiency for each digest is calculated by dividing the sum of the amounts of the 1800 and 1173 bp fragments by the sum of all fragments (2973, 1800 and 1173 bp). Note that the sizes of the products determined are only accurate to within 19% of the expected values and may thus vary from sample to sample. The results will also list a peak at 100 bp (the internal lower marker) and 170 bp of unknown origin. Those peaks should be ignored for data analysis.

Figure 2:
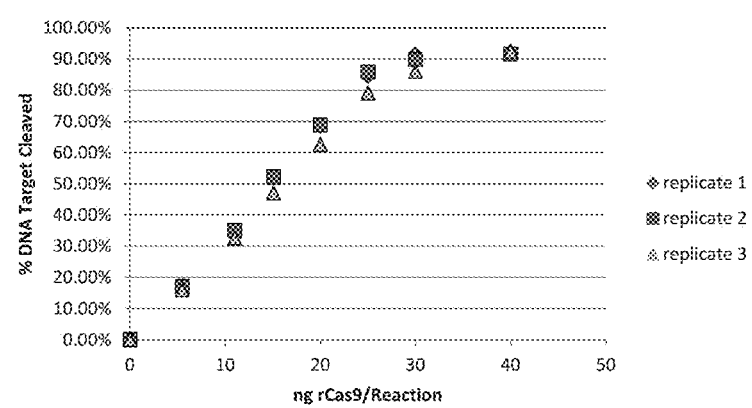
FIG. 2 is a graphical depiction of the image in FIG. 1.

For determination of the amount of Cas9 required for 50% digestion, plot the cleavage efficiency against the Cas9 input (ng Cas9/reaction) and determine the slope and y-intercept for the linear part of the plot. An example of such a plot is shown in FIG. 2. From this equation the Cas9 concentration required for 50% digestion can be directly determined. FIG. 3 shows data used to construct the graph of FIG. 2.

The calculation and graph are based on a triplicate assay. For determination of units/ng the slope and intercept of the data from 0-25 ng of Cas9 input were used. The ng/U were calculated as (0.5+intercept)/slope. The specific activity (in U/mg) is derived using the following formula:

$$SA\ (U/mg) = 1,000,000(ng/mg)/15.2\ (ng/U) = 65,789\ U/mg.$$

Example 2

Testing of Surfactants

Cas9 plasmid DNA cleavage assay: Linearized pKan-C1 plasmid DNA (100 ng [2.6 nM]) was incubated for 30 min at 30° C. with purified Cas9 protein (50-500 nM) and 50 nM guide RNA in a Cas9 plasmid cleavage buffer (50 mM Tris-HCl pH 7.0, 50 mM NaCl) with 2 or 10 mM $MgCl_2$. The reactions were stopped by heat inactivation of the enzyme at 65° C. for 15 minutes. Cleavage reactions were analyzed by Agilent Tape Station using Genomic Screen Tapes.

Figure 4:
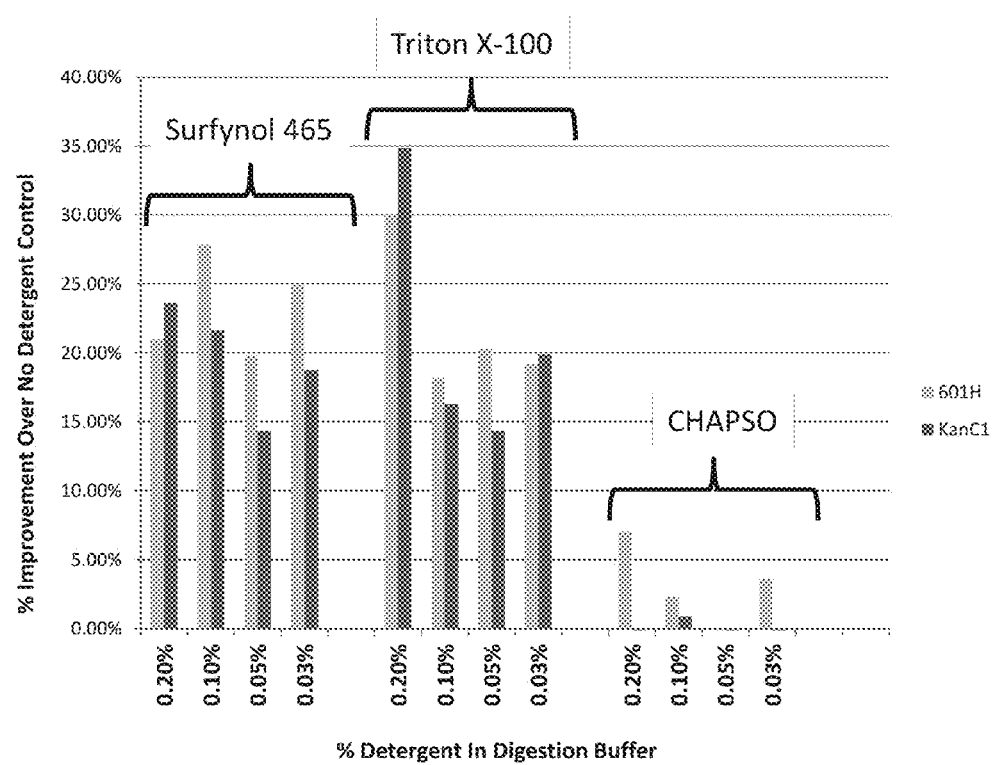
FIG. 4 is a graph showing the percent improvement of Cas9 cleavage efficiency in digestion buffer supplemented with detergent using two different RNA guides (data shown in Table 1).
Figure 5:
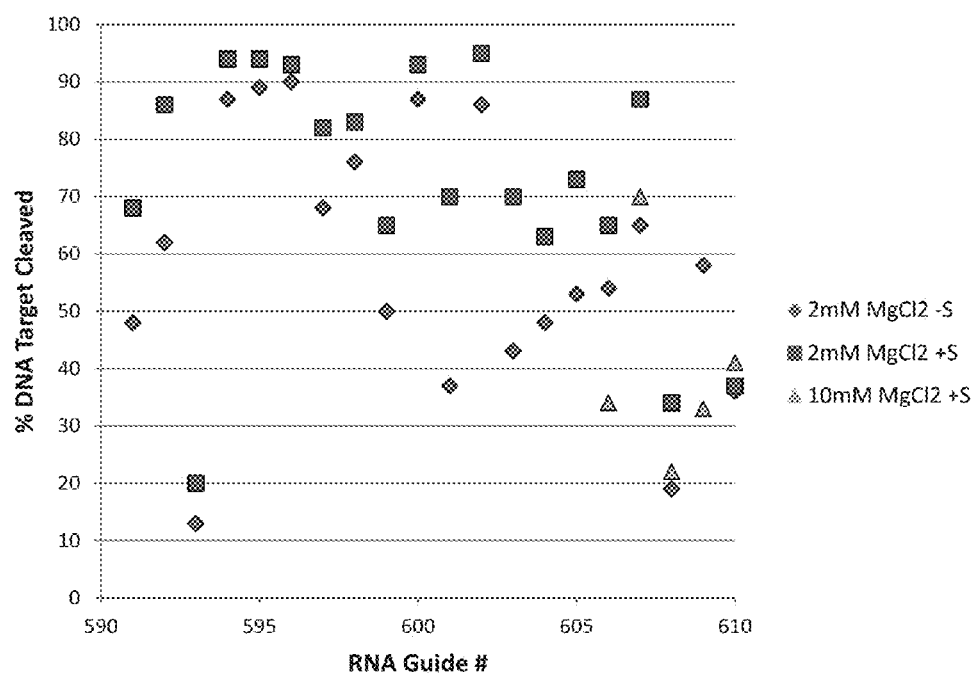
FIG. 5 is a table and corresponding plot showing a comparison of DNA template digestion with Cas9 as a function of variable RNA guides in the presence or absence of 0.025% Surfynol 465 ("Surf" in the table; "S" in the plot legend), and 2 mM or 10 mM $MgCl_2$.

It was discovered that a non-ionic, non-detergent surfactant Surfynol 465 and a non-ionic detergent Triton X-100 improved enzyme activity while a common Zwitterionic detergent CHAPSO had no effect on Cas9 activity (FIG. 4). In addition, at low Cas9 concentration, a variety of guide RNAs demonstrated improved performance in the presence of Surfynol 465 versus absence of the surfactant (FIG. 5). Cationic and anionic detergents were not tested.

Cas9 assays were performed in the following 1× digestion buffer to demonstrate the activity enhancing properties of the aforementioned surfactants/detergents: 100 mM Tris pH 7.0, 50 mM NaCl, 2 mM or 10 mM $MgCl_2$, various percentages of Surfynol-465, Triton X-100 or CHAPSO, various nanogram (ng) quantities of Cas9, and 50 nM guide RNA. Reaction mixtures were incubated at 30° C. for 30 minutes followed by heat inactivation of the enzyme. Table 1 lists the surfactants/detergents used at various concentrations and the resulting DNA template cleavage percentage.

TABLE 1

List of Surfactants/Detergents, Concentrations and Percent Cleavage of Substrate DNA.

| Detergent | % cleavage |
|---|---|
| Guide 601 | |
| None | 0.54 |
| None | 0.49 |
| None | 0.48 |
| Surf 465 0.2% | 0.60 |
| Surf 465 0.1% | 0.64 |
| Surf 465 0.05% | 0.60 |
| Surf 465 0.025% | 0.62 |
| Triton X 100 0.2% | 0.65 |
| Triton X 100 0.1% | 0.59 |
| Triton X 100 0.05% | 0.60 |
| Triton X 100 0.025% | 0.60 |
| Chapso 0.2% | 0.54 |
| Chapso 0.1% | 0.51 |
| Chapso 0.05% | 0.50 |
| Chapso 0.025% | 0.52 |
| Kan C1 Guide | |
| None | 0.46 |
| None | 0.44 |
| None | 0.44 |
| Surf 465 0.2% | 0.56 |
| Surf 465 0.1% | 0.55 |
| Surf 465 0.05% | 0.51 |
| Surf 465 0.025% | 0.53 |
| Triton X 100 0.2% | 0.61 |
| Triton X 100 0.1% | 0.52 |
| Triton X 100 0.05% | 0.51 |
| Triton X 100 0.025% | 0.54 |
| Chapso 0.2% | 0.44 |
| Chapso 0.1% | 0.45 |
| Chapso 0.05% | 0.43 |
| Chapso 0.025% | 0.43 |

Figure 6:
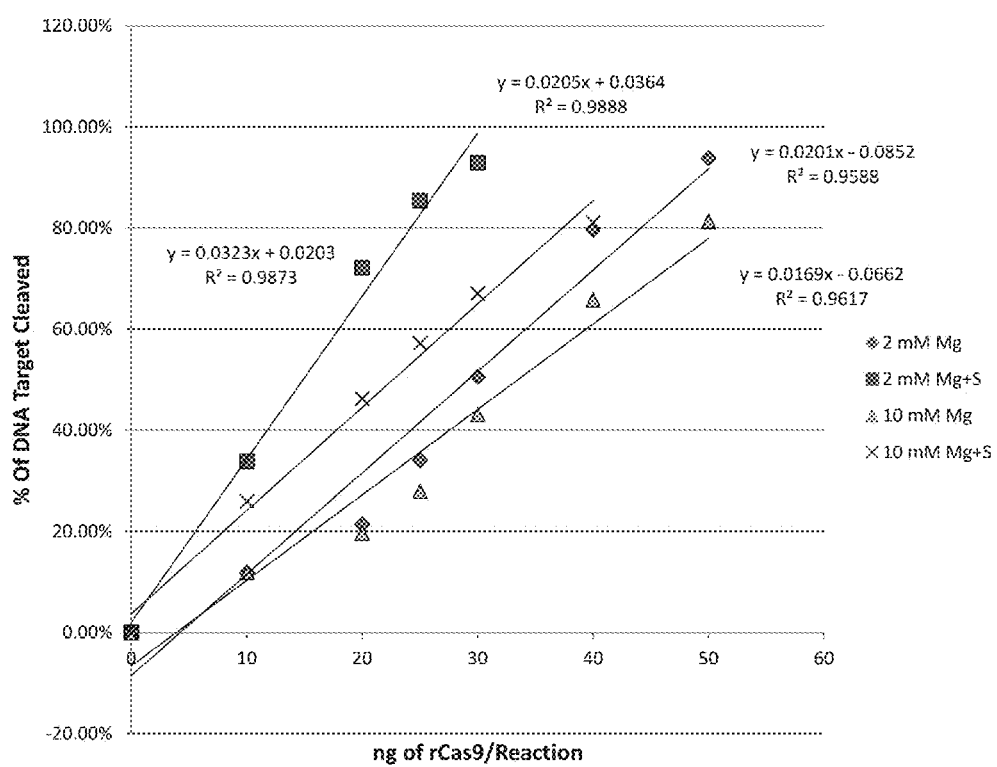
FIG. 6 is a graph showing the percent substrate cleaved by Cas9 in the presence of 2 and 10 mM $MgCl_2$ with and without 0.025% Surfynol 465 (S).

The raw data was transformed and plotted as shown in FIG. 4. The non-ionic surfactant Surfynol and the non-ionic surfactant Triton X-100 significantly increased Cas9 activity over the Zwitterionic detergent CHAPSO and in the absence of surfactants/detergents. FIG. 5 demonstrates that nineteen guide RNAs demonstrated improved efficiency in the presence of Surfynol 465 versus no surfactant. In only one case (Guide 610) the addition of surfactant had no demonstrable effect on improving guide RNA efficiency. FIG. 6 shows increased Cas9 activity in the presence of 0.025% Surfynol 465 at two concentrations of magnesium.

What is claimed is:

1. A reaction mixture for in vitro cleavage of a nucleic acid target comprising:
   a) a Cas9 protein;
   b) a guide RNA;
   c) a salt;
   d) a buffering agent;
   e) a nucleic acid target; and
   f) a non-ionic surfactant, wherein the non-ionic surfactant is a polyoxyethylene or polyoxypropylene surfactant, a glycosidic surfactant, or a bile salt surfactant;
   wherein components a)-f) are combined in vitro.

2. The reaction mixture of claim 1, wherein the buffering agent is selected from the group consisting of Tris, HEPES, TAPS, MOPS and MES.

3. The reaction mixture of claim 2, wherein the buffering agent is at a concentration of 1 mM to 50 mM.

4. The reaction mixture of claim 1, wherein the pH of the reaction mixture is in the range of pH 5 to 8.5.

5. The reaction mixture of claim 1, wherein the reaction mixture comprises one or more of NaCl, $MgCl_2$, $MgSO_4$ and KCl at a concentration in the range of 1 mM to 500 mM.

6. The reaction mixture of claim 5, wherein the reaction mixture comprises NaCl at a concentration of 10 mM to 250 mM and $MgCl_2$ at a concentration of 1 mM to 50 mM.

7. The reaction mixture of claim 1, wherein the presence of the surfactant increases the rate of cleavage of the nucleic acid target by at least 5%.

8. The reaction mixture of claim 1, wherein the non-ionic surfactant is present in the reaction mixture at a concentration in the range of 0.005% to 1%.

9. The reaction mixture of claim 1, wherein the non-ionic surfactant is a polyoxyethylene or polyoxypropylene surfactant.

10. The reaction mixture of claim 9, wherein the polyoxyethylene surfactant is a Brij series surfactant.

11. The reaction mixture of claim 9, wherein the polyoxyethylene surfactant is a Triton series surfactant.

12. The reaction mixture of claim 9, wherein the polyoxyethylene surfactant is a Tween series surfactant.

13. The reaction mixture of claim 9, wherein the polyoxyethylene surfactant is a Surfynol series surfactant.

14. The reaction mixture of claim 9, wherein the polyoxyethylene surfactant is a Tergitol series surfactant.

15. The reaction mixture of claim 1, wherein the non-ionic surfactant is a glycosidic surfactant.

16. The reaction mixture of claim 1, wherein the non-ionic surfactant is a bile salt surfactant.

17. A reaction mixture for in vitro cleavage of a nucleic acid target comprising:
  a) a Cas9 protein;
  b) a guide RNA;
  c) a salt;
  d) a buffering agent;
  e) a nucleic acid target; and
  f) a non-ionic surfactant, wherein the non-ionic surfactant has an HLB in the range of 12-15;
wherein components a)-f) are combined in vitro.

18. The reaction mixture of claim 17, wherein the non-ionic surfactant having an HLB in the range of 12-15 is selected from Triton X-100, Triton® SP-190, Triton XL-80N, Surfynol 465, Tergitol 15-S-7, 15-S-9, 15-S-12, Tergitol NP-9, Sulonic JL-80X, Ethofat 242/25, IGEPAL CA-720 and Lutensol NP 10.

19. A kit for preparing the reaction mixture of claim 1, comprising:
  a) a Cas9 protein; and
  b) a concentrated reaction buffer comprising salt, a buffering agent and a non-ionic surfactant, wherein the non-ionic surfactant is a polyoxyethylene or polyoxypropylene surfactant, a glycosidic surfactant, or a bile salt surfactant.

20. A kit for preparing the reaction mixture of claim 17, comprising:
  a) a Cas9 protein; and
  b) a concentrated reaction buffer comprising salt, a buffering agent and a non-ionic surfactant, wherein the non-ionic surfactant has an HLB in the range of 12-15.

* * * * *

UNITED STATES PATENT AND TRADEMARK OFFICE
CERTIFICATE OF CORRECTION

PATENT NO. : 9,850,521 B2
APPLICATION NO. : 14/727479
DATED : December 26, 2017
INVENTOR(S) : Jeffrey Carl Braman et al.

It is certified that error appears in the above-identified patent and that said Letters Patent is hereby corrected as shown below:

In Column 7, Line 9, delete "Sulonic" and insert -- Surfonic --, therefor.

In Column 8, Line 62, delete "Sulonic" and insert -- Surfonic --, therefor.

In Column 9, Line 16, delete "industries" and insert -- Industries --, therefor.

In Column 14, Line 8, in Claim 18, delete "Sulonic" and insert -- Surfonic --, therefor.

Signed and Sealed this
Twenty-ninth Day of May, 2018

Andrei Iancu
*Director of the United States Patent and Trademark Office*